United States Patent [19]

Weissmüller et al.

[11] Patent Number: 4,877,786
[45] Date of Patent: Oct. 31, 1989

[54] AMINOMETHYLISOXAZOLIDINES, FUNGICIDAL COMPOSITIONS AND USE

[75] Inventors: Joachim Weissmüller, Monheim; Dieter Berg, Wuppertal; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 130,375

[22] Filed: Dec. 8, 1987

[30] Foreign Application Priority Data

Dec. 22, 1986 [DE] Fed. Rep. of Germany ....... 3643942

[51] Int. Cl.$^4$ ............ A01N 43/80; A01N 43/84; C07D 261/08; C07D 413/06
[52] U.S. Cl. ................ 514/236.8; 514/212; 514/318; 514/326; 514/340; 514/343; 514/378; 540/597; 540/603; 544/124; 544/137; 546/193; 546/209; 546/275; 546/281; 548/240
[58] Field of Search ............... 540/597, 603; 544/124, 544/137; 546/193, 209, 275, 281; 548/240; 514/212, 236.8, 318, 326, 340, 343, 378

[56] References Cited

U.S. PATENT DOCUMENTS 4,678,797 1/1987 Ingendoh et al. .................. 514/378

FOREIGN PATENT DOCUMENTS 43-14215 6/1968 Japan.

Primary Examiner—Robert Ramsuer
Attorney, Agent, or Firm—Sprung Horn Kramer & Woods

[57] ABSTRACT

Fungicidally active aminomethyl-isoxazolidines of the

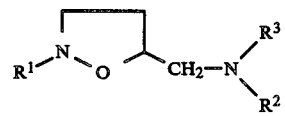

in which
$R^1$ represents optionally substituted alkyl, or represents optionally substituted cycloalkyl, or represents optionally substituted tetrahydronaphthyl, or represents optionally substituted decahydronaphthyl and
$R^2$ and $R^3$ independently of one another each represent hydrogen, or represent in each case optionally substituted alkyl, alkenyl, cycloalkyl or aryl, or together with the nitrogen atom to which they are bonded represent an optionally substituted saturated heterocyclic radical, which can optionally contain further hetero atoms, and acid addition salts thereof. Some intermediates therefor are also new.

8 Claims, No Drawings

AMINOMETHYLISOXAZOLIDINES, FUNGICIDAL COMPOSITIONS AND USE

The invention relates to new aminomethylisoxazolidines, several processes for their preparation and their use as agents for combating pests.

It is already known that certain isoxazolidines, such as, for example, 2-methyl-5-(2-pyridyl)-isoxazolidine or 5-(3,4-dichlorobenzyl)-5-ethoxycarbonyl-2-isopropyl-isoxazolidine or 5-benzyl-5-ethoxycarbonyl-2-t-butyl-isoxazolidine, have fungicidal properties. See U.S. Patent No. 4,678,797.

However, the activity of these already known compounds is not always completely satisfactory in all fields of use, especially when low amounts are applied and in the case of low concentrations.

New aminomethylisoxazolidines of the general formula (I)

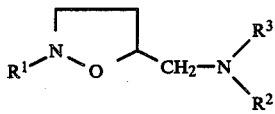

(I)

in which
$R^1$ represents optionally substituted alkyl, or represents optionally substituted cycloalkyl, or represents optionally substituted tetrahydronaphthyl, to or represents optionally substituted decahydronaphthyl and $R^2$ and $R^3$ independently of one another each represent hydrogen, or represent in each case optionally substituted alkyl, alkenyl, cycloalkyl, or aryl, or together with the nitrogen atom to which they are bonded represent an optionally substituted saturated heterocyclic radical, which can optionally contain further hetero atoms, and acid addition salts thereof, have been found.

Where appropriate, the compounds of the formula (I) can be obtained as geometric and/or optical isomers or isomer mixtures of varying composition. Both the pure isomers and the isomer mixtures are claimed according to the invention and are understood below by formula (I).

It has furthermore been found that the new aminomethylisoxazolidines of the general formula (I)

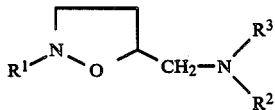

(I)

in which
$R^1$ represents optionally substituted alkyl, or represents optionally substituted cycloalkyl, or represents optionally substituted tetrahydronaphthyl, or represents optionally substituted decahydronaphthyl and $R^2$ and $R^3$ independently of one another each represent hydrogen, or represent in each case optionally substituted alkyl, alkenyl, cycloalkyl or aryl, or together with the nitrogen atom to which they are bonded represent an optionally substituted saturated heterocyclic radical, which can optionally contain further hetero atoms, and acid addition salts thereof, are obtained by a process in which (a) hydroxylamine derivatives of the formula (II)

$$R^1-NH-OH \quad (II)$$

in which $R^1$ has the abovementioned meaning, are reacted with allylamines of the formula (III)

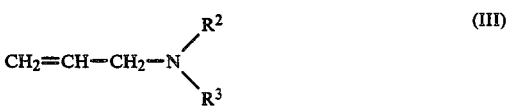

(III)

in which $R^2$ and $R^3$ have the abovementioned meaning, in the presence of formaldehyde and if appropriate in the presence of a diluent, or by a process in which (b) isoxazolidines of the formula (IV)

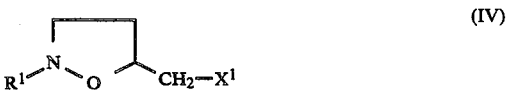

(IV)

in which
$R^1$ has the abovementioned meaning and
$X^1$ represents an electron-withdrawing leaving group,
are reacted with amines of the formula (V)

(V)

in which $R^2$ and $R^3$ have the abovementioned meaning, if appropriate in the presence of a diluent and if appropriate in the presence of an acid-binding agent, and if appropriate in the presence of a catalyst, or by a process in which (c) the aminomethylisoxazolidines obtainable by process (a) or (b), of the formula (Ia)

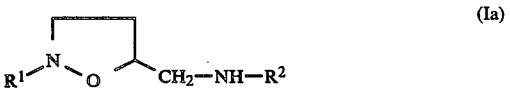

(Ia)

in which $R^1$ and $R^2$ have the abovementioned meaning, are reacted with alkylating agents of the formula (VI)

$$R^{3-1}-X^2 \quad (VI)$$

in which
$R^{3-1}$ represents in each case optionally substituted alkyl, alkenyl or cycloalkyl and $X^2$ represents an electron-withdrawing leaving group,
if appropriate in the presence of a diluent and if appropriate in the presence of an acid-binding agent, and if appropriate in the presence of a catalyst, and, if appropriate, an acid is then added on.

Finally, it has been found that the new aminomethylisoxazolidines have fungicidal properties.

Surprisingly, the aminomethylisoxazolidines according to the invention exhibit a considerably better fungicidal activity than the isoxazolidines known from the prior art, such as, for example, 2-methyl-5-(2-pyridyl)-isoxazolidine or 5-(3,4-dichlorobenzyl)-5-ethoxycarbonyl-2-isopropyl-isoxazolidine or 5-benzyl-5-ethoxycarbonyl-2t-butyl-isoxazolidine, which are closely related compounds chemically and from the point of view of their action.

Formula (I) provides a general definition of the aminomethylisoxazolidines according to the invention. Preferred compounds of the formula (I) are those in which $R^1$ represents in each case straight-chain or branched alkyl, hydroxyalkyl, fluoroalkyl, alkoxyalkyl or fluoroalkoxyalkyl with in each case 1 to 18 carbon atoms and, where appropriate, 1 to 9 fluorine atoms, or represents arylalkyl, aryloxyalkyl or arylthioalkyl with in each case 6 to 10 carbon atoms in the aryl part and 1 to 10 carbon atoms in the straight-chain or branched alkyl part, optionally monosubstituted or polysubstituted in the aryl part by identical or different substituents, possible substituents on the aryl in each case being: halogen, cyano, nitro, in each case straight-chain or branched alkyl, alkoxy, alkylthio, halogenoalkyl, halogenoalkoxy and halogenoalkylthio with in each case 1 to 6 carbon atoms and where appropriate 1 to 9 identical or different halogen atoms, amino and in each case straight-chain or branched alkylamino, dialkylamino and alkoximinoalkyl with in each case 1 to 4 carbon atoms in the individual alkyl parts; or represents cycloalkylalkyl or cycloalkyl with in each case 3 to 10 carbon atoms in the cycloalkyl part and where appropriate 1 to 6 carbon atoms in the straight-chain or branched alkyl part and in each case optionally monosubstituted or polysubstituted in the cycloalkyl part by identical or different substituents, possible substituents in each case being: hydroxyl and in each case straight-chain or branched alkyl, alkoxy, halogenoalkyl and halogenoalkoxy with in each case 1 to 6 carbon atoms and where appropriate 1 to 9 identical or different halogen atoms; or, finally, represents tetrahydronaphthyl or decahydronaphthyl, in each case optionally monosubstituted or polysubstituted by identical or different substituents, possible substituents in each case being: halogen and in each case straight-chain or branched alkyl, alkoxy, alkylthio, halogenoalkyl, halogenoalkoxy, halogenoalkylthio and alkoximinoalkyl with in each case 1 to 4 carbon atoms and where appropriate 1 to 9 identical or different halogen atoms and $R^2$ and $R^3$ independently of one another each represent hydrogen, or represent in each case straight-chain or branched alkyl with 1 to 8 carbon atoms, hydroxyalkyl with 2 to 8 carbon atoms or alkoxyalkyl with 3 to 8 carbon atoms, or represent straight-chain or branched alkenyl with 3 to 8 carbon atoms, or represent cycloalkyl which has 3 to 7 carbon atoms and is in each case optionally monosubstituted or polysubstituted by identical or different substituents from the group comprising alkyl with 1 to 4 carbon atoms and/or halogen, or represent aralkyl or aryl with 6 to 10 carbon atoms in the aryl part and where appropriate 1 to 4 carbon atoms in the straight-chain or branched alkyl part and in each case optionally monosubstituted or polysubstituted in the aryl part by identical or different substituents, possible substituents in each case being: halogen, cyano, nitro and in each case straight-chain or branched alkyl, alkoxy, alkylthio, halogenoalkyl, halogenoalkoxy, halogenoalkylthio and alkoximinoalkyl with in each case 1 to 4 carbon atoms in the individual alkyl parts and where appropriate 1 to 9 identical or different halogen atoms, or $R^2$ and $R^3$, together with the nitrogen atom to which they are bonded, represent a saturated 5-to 7-membered heterocyclic radical which optionally can contain further hetero atoms, in particular nitrogen, oxygen and/or sulphur, and is optionally monosubstituted or polysubstituted by identical or different substituents, possible substituents being: in each case straight-chain or branched alkyl or hydroxyalkyl with in each case 1 to 4 carbon atoms.

Particularly preferred compounds of the formula (I) are those in which $R^1$ represents straight-chain or branched alkyl with 1 to 12 carbon atoms; or represents phenylalkyl, phenoxyalkyl or phenylthioalkyl with in each case 1 to 8 carbon atoms in the particular straight-chain or branched alkyl parts and optionally mono-, di- or trisubstituted in the phenyl part by identical or different substituents, possible substituents on the phenyl in each case being: fluorine, chlorine, bromine, straight-chain or branched alkyl with 1 to 6 carbon atoms, methoxy, ethoxy, n- or i-propoxy, n-, i-, s- or t-butoxy, methylthio, trifluoromethyl, trifluoromethoxy, trifluoromethylthio and methoximinomethyl; or represents cycloalkylalkyl or cycloalkyl with in each case 5, 6 or 10 carbon atoms in the cycloalkyl part and where appropriate 1 to 4 carbon atoms in the alkyl part and in each case optionally mono-, di- or trisubstituted in the cycloalkyl part by identical or different substituents, possible substituents in each case being: straight-chain or branched alkyl with 1 to 5 carbon atoms; or represents decahydronaphthyl which is optionally mono-, di- or trisubstituted by identical or different substituents, substituents which may be mentioned being: straight-chain or branched alkyl with 1 to 5 carbon atoms, or, finally, represents tetrahydronaphthyl which is optionally mono-, di- or trisubstituted by identical or different substituents, possible substituents being: straight-chain or branched alkyl with 1 to 5 carbon atoms, methoxy, trifluoromethyl, trifluoromethoxy and chlorine, and $R^2$ and $R^3$ independently of one another each represent hydrogen, methyl, ethyl, n- or i-propyl, n-, i-, s- or t-butyl, n- or i-pentyl, n- or i-hexyl, allyl, n- or i-butenyl, n- or i-pentenyl, hydroxypropyl, methoxyethyl, ethoxyethyl, methoxypropyl, ethoxypropyl or propoxypropyl, or represent cyclopropylmethyl or dichlorocyclopropylmethyl, or represent dichlorodimethylcyclopropylmethyl, or represent dimethylcyclopropylmethyl or cyclohexyl, or $R^2$ and $R^3$, together with the nitrogen atom to which they are bonded, represent a heterocyclic radical of the formula

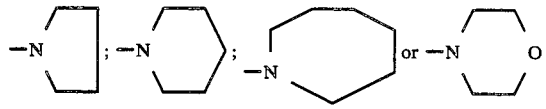

which is optionally mono-, di- or trisubstituted by identical or different substituents, possible substituents being: methyl, ethyl and hydroxymethyl.

Addition products of acids and those aminomethylisoxazolidines of the formula (I) in which the substituents $R^1$, $R^2$ and $R^3$ have the meaning which have already been given as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono-, bi- and trifunctional carboxylic acids and hydrocarboxylic acids, such as, for example, acetic acid, maleic acid, succinic acid, fumaric acid, tartaric acid, citric acid, salicylic acid, sorbic acid and lactic acid, and furthermore sulphonic acids, such as p-toluenesulphonic acid and 1,5-naphthalenedisulphonic acid, as well as saccharin.

The following aminomethylisoxazolidines of the general formula (I) may be mentioned specifically, in addition to the compounds mentioned in the preparation examples:

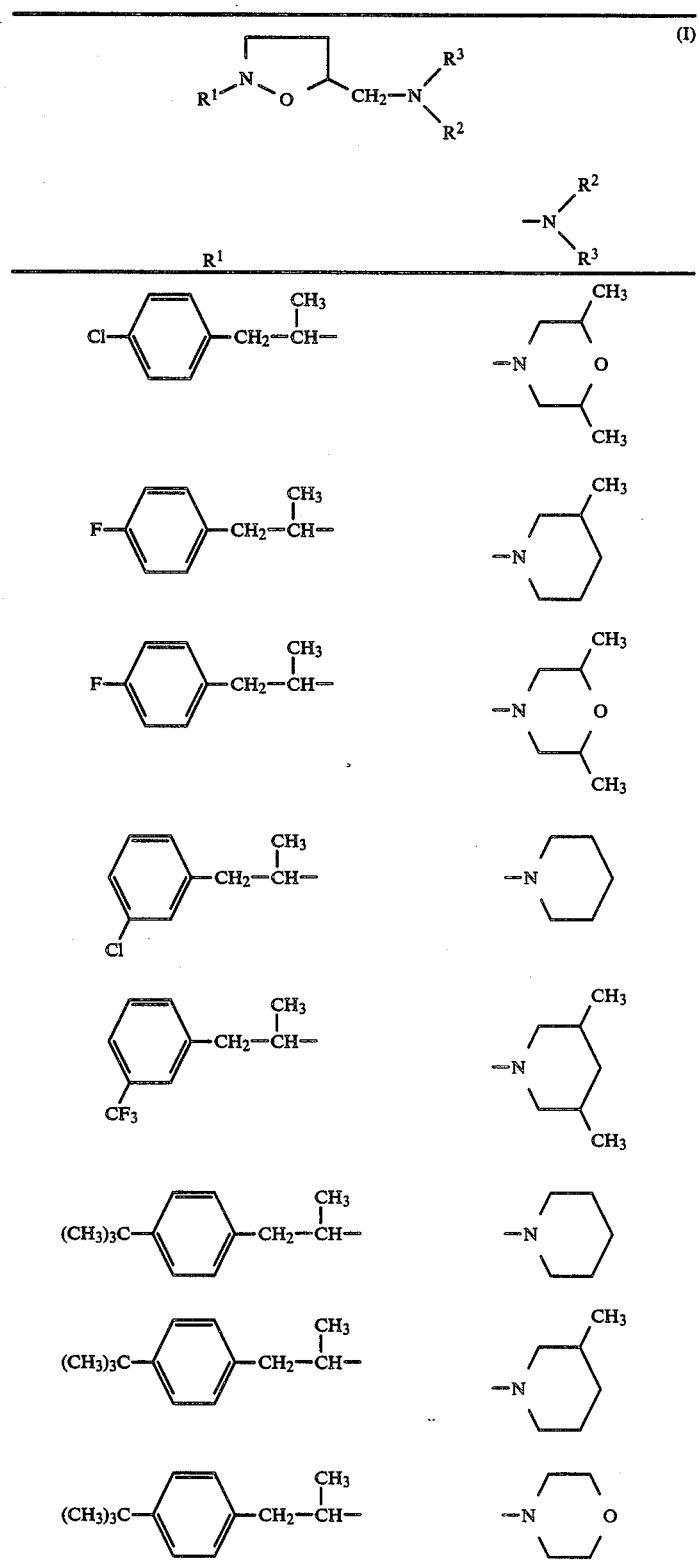

-continued
$$\begin{array}{c} R^1 \diagdown N \diagup \diagdown \\ O \diagdown CH_2-N \diagdown R^3 \\ R^2 \end{array} \quad (I)$$
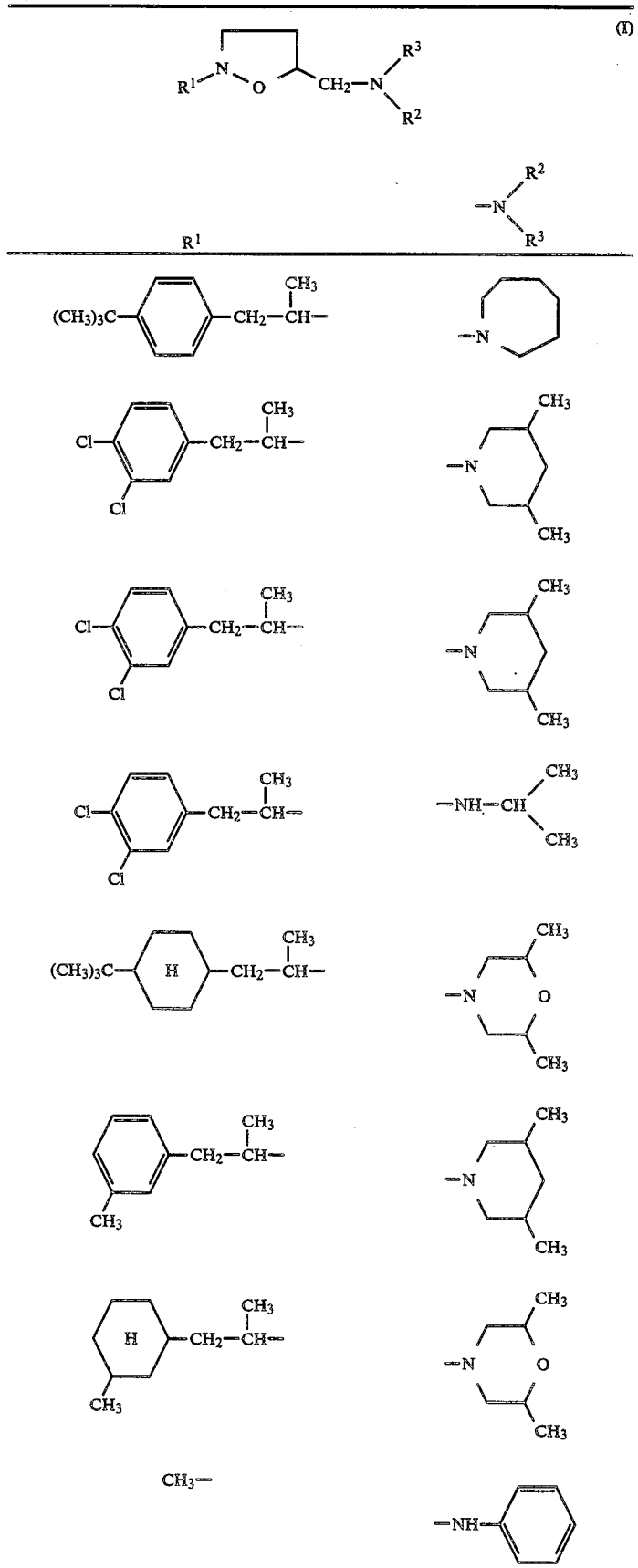

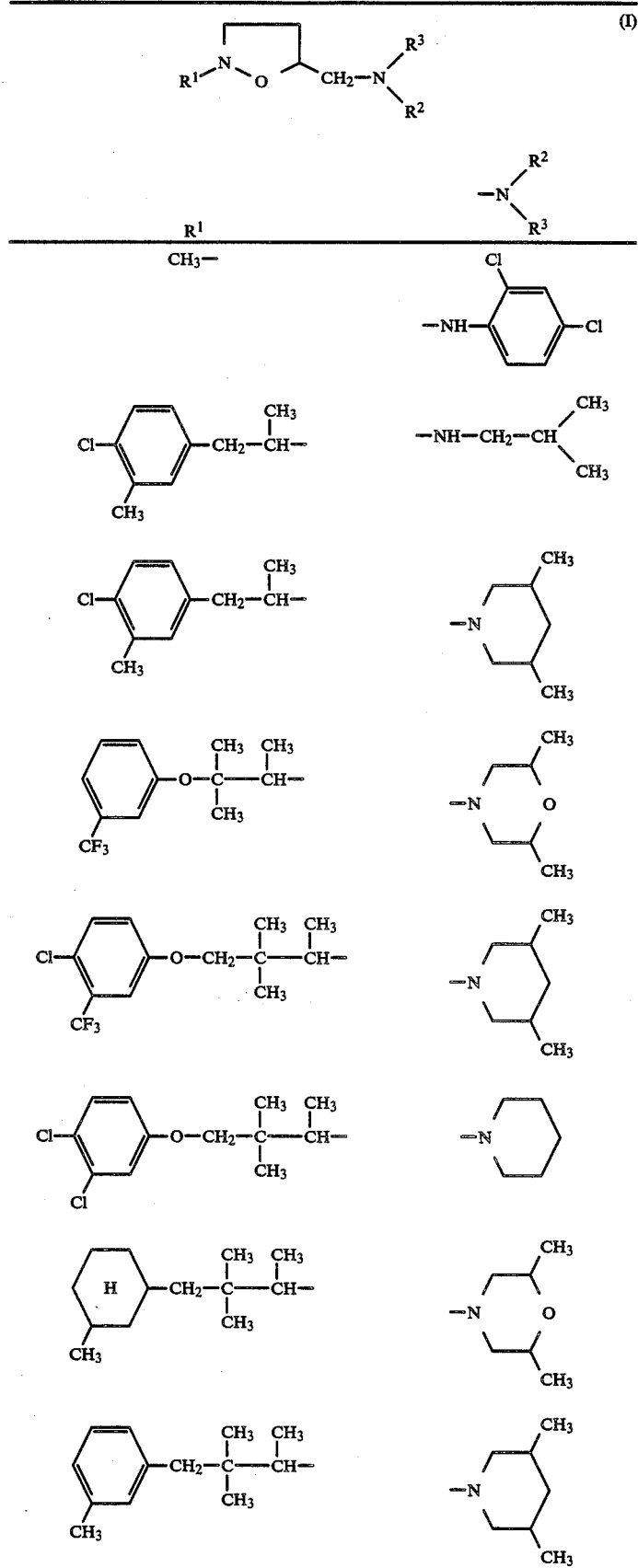

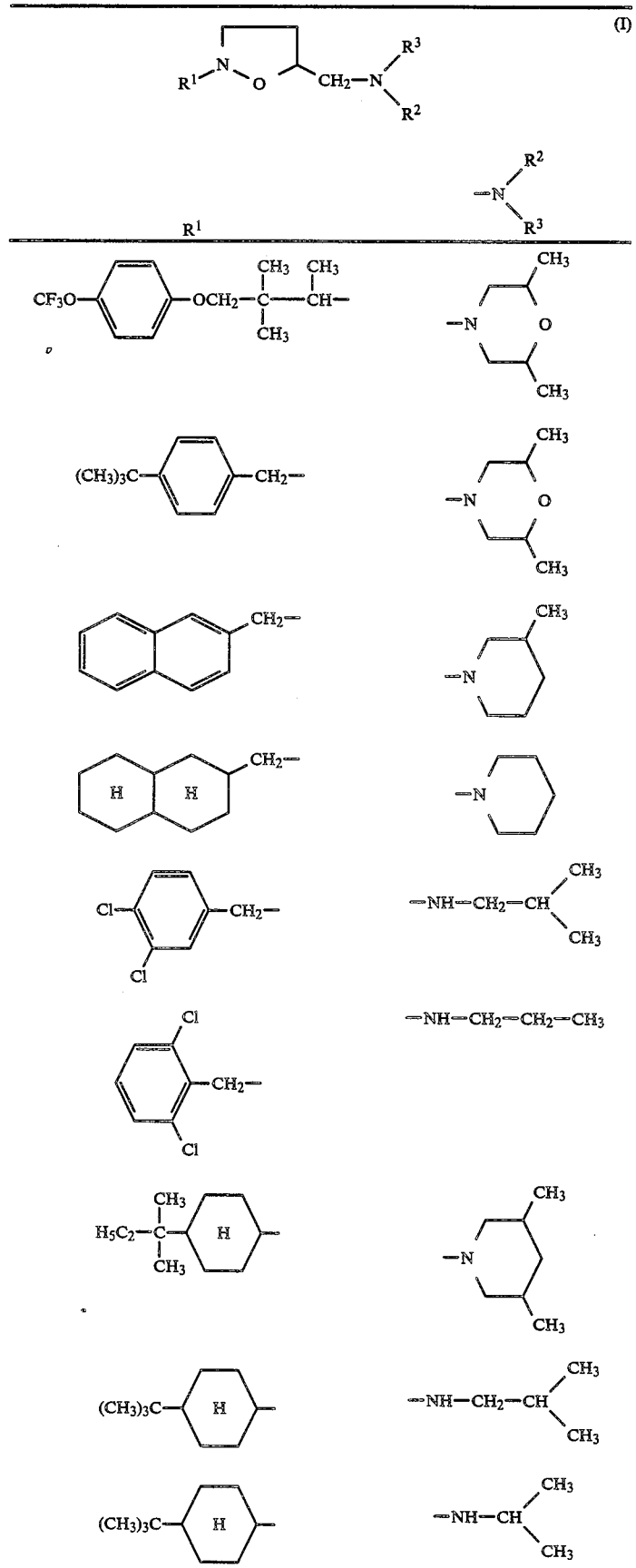

-continued $$R^1-N\diagdown O \diagup CH_2-N\diagup R^3 \diagdown R^2 \qquad (I)$$

| $R^1$ | $-N\diagup R^2 \diagdown R^3$ |
|---|---|
| 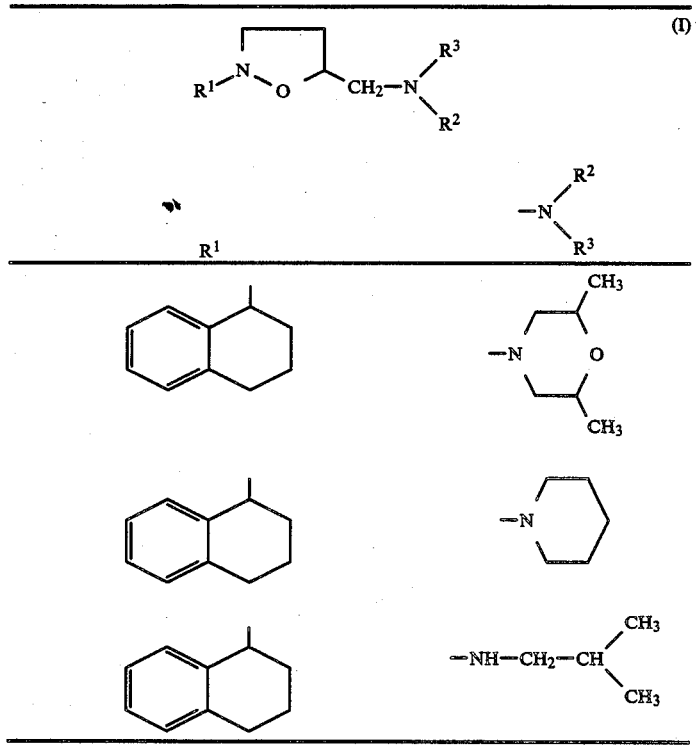 | |

If, for example, N-[3-(3,4-dichlorophenyl)-2,2-dimethylpropyl]-hydroxylamine, formaldehyde and N-allylpiperidine are used as starting substances, the course of the reaction in process (a) according to the invention can be represented by the following equation:

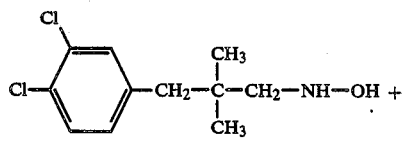

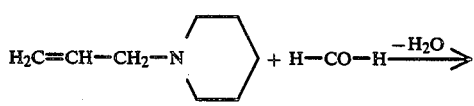

-continued

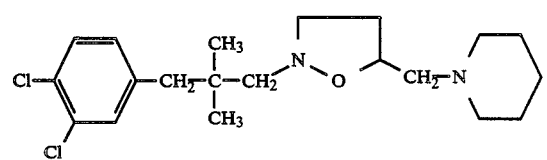

If, for example, 2-[4-(4-fluorophenoxy)-3,3-dimethylbut-2-yl]-5-bromomethylisoxazolidine and 3-methylpiperidine are used as starting substances, the course of the reaction in process (b) according to the invention can be represented by the following equation:

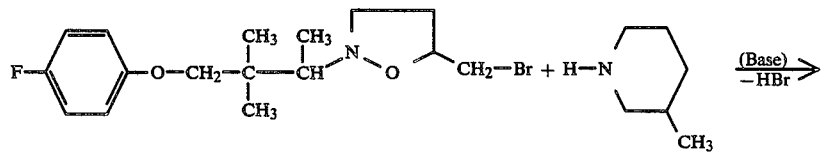

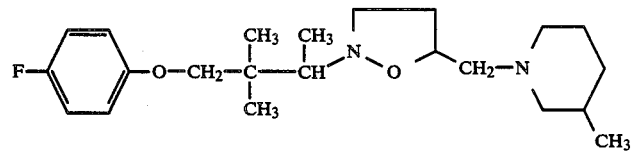

If, for example, 2-cyclohexyl-5-aminomethylisoxazolidine and methyl iodide are used as starting substances, the course of the reaction in process (c) according to the invention can be represented by the following equation:

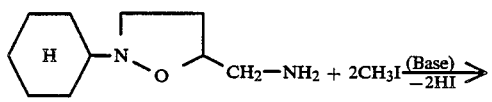

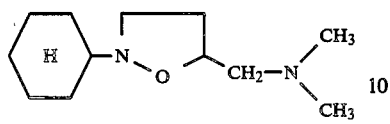

Formula (II) provides a general definition of the hydroxylamine derivatives required as starting substances for carrying out process (a) according to the invention. In this formula (II), $R^1$ preferably represents those radicals which have already been mentioned as preferred for this substituent in connection with the description of the substances of the formula (I) according to the invention.

The hydroxylamine derivatives of the formula (II) are known in most cases (compare, for example, Tetrahedron 31, 1531-1535 [1975]; Chem. Pharm. Bull. 29, 1615-1623 [1981]; DE-OS (German Published Specification) 2,337,021; Z. Naturforsch. 19b, 1021-1026 [1964]; Chem. Ber. 92, 63-70 [1959]; German Patent No. 950,369 [1956]; DE-OS (German Published Specification) 3,418,395).

Hydroxylamines which are not yet known are those of the formula (IIa)

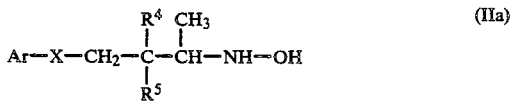

in which

Ar represents optionally substituted phenyl, possible substituents being: halogen, cyano, nitro, in each case straight-chain or branched alkyl, alkoxy, alkylthio, halogenoalkyl, halogenoalkoxy and halogenoalkylthio with in each case 1 to 6 carbon atoms and where appropriate 1 to 9 identical or different halogen atoms, amino and in each case straight-chain or branched alkylamino, dialkylamino and alkoximinoalkyl with in each case 1 to 4 carbon atoms in the individual alkyl parts;

X represents oxygen or sulphur and $R^4$ and $R^5$ independently of one another each represent alkyl, in particular methyl, ethyl or i-propyl.

The known hydroxylamine derivatives of the formula (II) and also those which are not yet known can be obtained by a process analogous to known processes, for example by a procedure in which aldehydes or ketones of the formula (VII)

in which $R^6$ represents optionally substituted alkyl and $R^7$ represents optionally substituted alkyl or hydrogen, or $R^6$ and $R^7$, together with the carbon atom on which they are positioned, represent optionally substituted cycloalkyl, or represent optionally substituted tetrahydronaphthyl, or represent optionally substituted decahydronaphthyl;

are reacted with hydroxylamine hydrochloride, if appropriate in the presence of a base, such as, for example, sodium hydroxide, and if appropriate in the presence of a diluent, such as, for example, water, at temperatures between 10° C. and 100° C., and the oximes thus obtainable, of the formula (VIII)

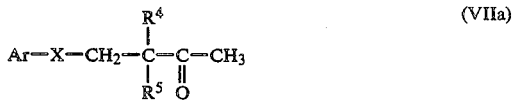

in which $R^6$ and $R^7$ have the abovementioned meaning, are reduced in a second stage with reducing agents, such as, for example, sodium cyano-borohydride, if appropriate in the presence of a diluent, such as, for example, methanol, at temperatures between 0° C. and 50° C. (compare also the preparation examples).

The keytones and aldehydes of the formula (VII) are generally known compounds of organic chemistry. The ketones of the formula (VIIa)

in which

Ar, X, $R^4$ and $R^5$ have the abovementioned meaning, which are required for the preparation of the hydroxylamine derivatives which are not yet known, of the formula (IIa), are likewise known (compare, for example, DE-OS (German Published Specification) 3,210,725 or DE-OS (German Published Specification) 3,048,266).

Formula (VII) provides a definition of the aldehydes and ketones. Preferably, in this formula, $R^6$ represents in each case straight-chain or branched alkyl, hydroxyalkyl, fluoroalkyl, alkoxyalkyl or fluoroalkoxyalkyl with in each case 1 to 17 carbon atoms and where appropriate 1 to 9 fluorine atoms, or represent arylalkyl, aryloxyalkyl or arylthioalkyl with in each case 6 to 10 carbon atoms in the aryl part and 1 to 10 carbon atoms in the aryl part and 1 to 10 carbon atoms in the straight-chain or branched alkyl part, optionally monosubstituted or polysubstituted in the alkyl part by identical or different substituents, possible substituents on the aryl in each case being: halogen, cyano, nitro, in each case straight-chain or branched alkyl, alkoxy, alkylthio, halogenoalkyl, halogenoalkoxy and halogenoalkylthio with in each case 1 to 6 carbon atoms and where appropriate 1 to 9 identical or different halogen atoms, amino and in each case straight-chain or branched alkylamino, dialkylamino or alkoximinoalkyl with in each case 1 to 4 carbon atoms in the individual alkyl parts; or represents cycloalkylalkyl which has 3 to 10 carbon atoms in the cycloalkyl part and where appropriate 1 to 5 carbon atoms in the straight-chain or branched alkyl part and is optionally monosubstituted or polysubstituted in the cycloalkyl part by identical or different substituents, possible substituents in each case being: hydroxyl and in each case straight-chain or branched alkyl, alkoxy, halogenoalkyl and halogenoalkoxy with in each case 1 to 6 carbon atoms and where appropriate 1 to 9 identical or different halogen atoms; and R⁷ has the meaning of R⁶, or is hydrogen, or R⁶ and R⁷, together with the carbon atom on which they are located, form a cycloalkyl radical with 3 to 10 carbon atoms, or form a tetrahydronaphthyl or decahydronaphthyl ring, in each case optionally monosubstituted or polysubstituted by identical or different substituents, possible substituents in each case being: halogen and in each case straight-chain or branched alkyl, alkoxy, alkylthio, halogenoalkyl, halogenoalkoxy, halogenoalkylthio and alkoximinoalkyl with in each case 1 to 4 carbon atoms and where appropriate 1 to 9 identical or different halogen atoms.

Particularly preferred compounds of the formula (VII) are those in which

R⁶ represents straight-chain or branched alkyl with 1 to 11 carbon atoms; or represents phenylalkyl, phenoxyalkyl or phenylthioalkyl with in each case 1 to 7 carbon atoms in the particular straight-chain or branched alkyl parts and optionally mono-, di- or trisubstituted in the phenyl part by identical or different substituents, possible substituents in each case being: fluorine, chlorine, bromine, straight-chain or branched alkyl with 1 to 6 carbon atoms, methoxy, ethoxy, n- or i-propoxy, n-, i-, s- or t-butoxy, methylthio, trifluoromethyl, trifluoromethoxy, trifluoromethylthio and methoximinomethyl; or represents cycloalkylalkyl which has 5, 6 or 10 carbon atoms in the cycloalkyl part and 1 to 3 carbon atoms in the alkyl part and is optionally mono-, di- or trisubstituted in the cycloalkyl part by identical or different substituents, possible substituents being: straight-chain or branched alkyl with 1 to 5 carbon atoms; and R⁷ has the meaning given for R⁶, or represents hydrogen, or R⁶ and R⁷, together with the carbon atom on which they are located, form a cycloalkyl radical which has 5, 6 or 10 carbon atoms and can be mono-, di- or trisubstituted by identical or different straight-chain or branched alkyl radicals with 1 to 5 carbon atoms; or form a decahydronaphthyl ring which is optionally mono-, di-or trisubstituted by identical or different substituents, substituents which may be mentioned being: straight-chain or branched alkyl with 1 to 5 carbon atoms; or, finally, form a tetrahydronaphthyl ring which is optionally mono-, di- or trisubstituted by identical or different substituents, possible substituents being: straight-chain or branched alkyl with 1 to 5 carbon atoms, methoxy, trifluoromethyl, trifluoromethoxy and chlorine.

Formula (III) provides a general definition of the allylamines furthermore required as starting substances for carrying out process (a) according to the invention. In this formula (III), R² and R³ preferably represent those radicals which have already been mentioned as preferred for these substituents in connection with the description of the substances of the formula (I) according to the invention.

The allylamines of the formula (III) are likewise generally known compounds of organic chemistry.

Formula (IV) provides a general definition of the isoxazolidines required as starting substances for carrying out process (b) according to the invention. In this formula (IV), R¹ preferably represents those radicals which have already been mentioned as preferred for this substituent in connectin with the description of the substances of the formula (I) according to the invention.

X¹ preferably represents halogen, in particular chlorine or bromine, or represents optionally substituted alkylsulphonyloxy or arylsulphonyloxy, such as, for example, methanesulphonyloxy or p-toluenesulphonyloxy.

The isoxazolidines of the formula (IV) are not yet known. They are obtained by a process analogous to process (a) according to the invention, by a procedure in which hydroxylamine derivatives of the formula (II)

  (II)

in which R¹ has the abovementioned meaning, are reacted with allyl halides or allyl alcohol of the formula (IX)

  (IX)

in which X³ represents hydroxyl or halogen, in particular hydroxyl, chlorine or bromine, in the presence of formaldehyde and if appropriate in the presence of a diluent, such as, for example, methanol or carbon tetrachloride, at temperatures between 20° C. and 80° C., and in cases where X³ represents hydroxyl, the hydroxymethylisoxazolidines thus obtainable, of the formula (X)

  (X)

in which R¹ has the abovementioned meaning, are reacted in a second stage with sulphonyl halides of the formula (XI)

  (XI)

in which

X⁴ represents halogen, in particular chlorine or bromine, and

R⁴ represents optionally substituted alkyl or aryl, such as, for example, methyl or p-tolyl, if appropriate in the presence of a diluent, such as, for example, methylene chloride, and if appropriate in the presence of a basic reaction auxiliary, such as, for example, triethylamine, at temperatures between 10° C. and 60° C.

The allyl halides and allyl alcohol of the formula (IX) and the sulphonyl halides of the formula (XI) are generally known compounds of organic chemistry.

Formula (V) provides a general definition of the amines furthermore required as starting substances for carrying out process (b) according to the invention. In this formula (V), R² and R³ represent those radicals which have already been mentioned as preferred for these substituents in connection with the description of the substances of the formula (I) according to the invention.

The amines of the formula (V) are likewise generally known compounds of organic chemistry.

Formula (Ia) provides a general definition of the aminomethylisoxazolidines required as starting substances for carrying out process (c) according to the invention. In this formula (Ia), R¹ and R² represent those radicals which have already been mentioned for these substituents in connection with the description of the substances of the formula (I) according to the invention.

The aminomethylisoxazolidines of the formula (Ia) are compounds according to the invention and are obtainable with the aid of processes (a) and (b) according to the invention.

Formula (VI) provides a general definition of the alkylating agents furthermore required as starting substances for carrying out process (c) according to the invention. In this formula (VI), $R^{3-1}$ preferably represents straight-chain or branched alkyl with 1 to 8 carbon atoms, or represents hydroxyalkyl with 2 to 8 carbon atoms or alkoxyalkyl with 3 to 8 carbon atoms, or represents straight-chain or branched alkenyl with 3 to 8 carbon atoms, or represents cycloalkyl or cycloalkylalkyl with in each case 3 to 7 carbon atoms in the cycloalkyl part and where appropriate 1 to 3 carbon atoms in the alkyl part, in each case optionally monosubstituted or polysubstituted by identical or different substituents from the group comprising alkyl with 1 to 4 carbon atoms and/or halogen, or represents aralkyl which has 6 to 10 carbon atoms in the aryl part and 1 to 4 carbon atoms in the straight-chain or branched alkyl part and is optionally monosubstituted or polysubstituted in the aryl part by identical or different substituents, substituents which may be mentioned being: halogen, cyano, nitro and in each case straight-chain or branched alkyl, alkoxy, alkylthio, halogenoalkyl, halogenoalkoxy, halogenoalkylthio and alkoximinoalkyl with in each case 1 to 4 carbon atoms in the individual alkyl parts and where appropriate 1 to 9 identical or different halogen atoms. $R^{3-1}$ represents, in particular, methyl, ethyl, n- or i-propyl, n-, i-, s- or t-butyl, n- or i-pentyl, n- or i-hexyl, allyl, n- or i-butenyl, n- or i-pentenyl, hydroxypropyl, methoxyethyl, ethoxyethyl, methoxpropyl, ethoxypropyl and propoxypropyl, or represents cyclopropylmethyl, dichlorocyclopropylmethyl, dimethylcyclopropylmethyl or dichlorodimethylcyclopropylmethyl. $X^2$ preferably represents halogen, in particular chlorine or bromine, or represents optionally substituted alkylsulphonyloxy or arylsulphonyloxy, such as, for example, methanesulphonyloxy or p-toluenesulphonyloxy. The alkylating agents of the formula (VI) are likewise generally known compounds of organic chemistry.

Possible diluents for carrying out process (a) according to the invention are inert organic solvents or mixtures thereof with water.

These include, in particular, aliphatic or aromatic, optionally halogenated hydrocarbons, such as, for example, cyclohexane, methylene chloride, chloroform and carbon tetrachloride, ethers, such as dioxane, tetrahydrofuran or ethylene glycol dimethyl or diethyl ether, amides, such as dimethylformamide, dimethylacetamide, N-methylformanilide, N-methylpyrrolidone or hexamethylphosphoric acid triamide, sulphoxides, such as dimethyl sulphoxide, or alcohols, such as methanol, ethanol or propanol, and mixtures thereof with water.

The reaction temperatures can be varied within a substantial range in carrying out process (a) according to the invention. The reaction is in general carried out at temperatures between 20° C. and 150° C., preferably at temperatures between 40° C. and 140° C.

For carrying out process (a) according to the invention, in general 0.8 to 1.3 mols, preferably equimolar amounts, of allylamine of the formula (III) and 1.0 to 5.0 mols of formaldehyde are employed per mol of hydroxylamine derivative of the formula (II).

It is also possible to use the hydroxylamine derivative of the formula (II) in the form of a hydrohalide salt, in particular of a hydrochloride. In this case, it is advantageous to add an equimolar amount of a suitable acid-binding agent, such as, for example, sodium hydroxide, sodium carbonate, potassium carbonate or triethylamine. An appropriate excess of allylamine of the formula (III) is also possible as the acid-binding agent. In addition, it is likewise possible to use the formaldehyde as an aqueous formalin solution.

The reaction is carried out and the reaction products of the formula (I) are worked up and isolated with the aid of customary methods analogous to known processes (compare also DE-OS (German Published Specification) 3,418,395 and the preparation examples).

Possible diluents for carrying out processes (b) and (c) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethyl sulphoxide.

If appropriate, processes (b) and (c) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyldimethyl-ammonium methyl-sulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride. It is also possible for processes (b) and (c) according to the invention to be carried out without the addition of a solvent.

Possible acid-binding agents for carrying out processes (b) and (c) according to the invention are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

It is also possible for the amines of the formulae (V) and (Ia) used as participants in the reaction to be used simultaneously in an appropriate excess as the acid-binding agent.

The reaction temperatures can be varied within a substantial range in carrying out processes (b) and (c) according to the invention. The reaction is in general carried out at temperatures between −20° C. and +150° C., preferably at temperatures between 0° C. and +120° C.

To carry out process (b) according to the invention, in general 1.0 to 3.0 mols, preferably 1.0 to 1.5 mols, of amine of the formula (V) and if appropriate 1.0 to 3.0 mols, preferably 1.0 to 1.5 mols, of acid-binding agent, and if appropriate 0.1 to 1.0 mol of phase transfer catalyst are employed per mol of isoxazolidine of the formula (IV).

For carrying out process (c) according to the invention, in general 1.0 to 5.0 mols, preferably 1.0 to 2.0 mols, of alkylating agent and 1.0 to 5.0 mols, preferably 1.0 to 2.0 mols, of acid-binding agent, and if appropriate 0.1 to 1.0 mol of phase transfer catalyst are employed per mol of aminomethylisoxazolidine of the formula (Ia).

In both cases, the reaction is carried out and the reaction products of the formula (I) are worked up and isolated by customary methods.

The following acids can preferably be used to prepare acid addition salts of the compounds of the formula (I): hydrogen halide acids, such as, for example, hydrochloric acid and hydrobromic acid, in particular hydrochloric acid, and furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid, as well as saccharin.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

The active compounds according to the invention have a powerful action against pests and can be used in practice for combating undesirable harmful organisms. The active compounds are suitable for use, inter alia, as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humili* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera Leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention thereby exhibit a particularly broad fungicidal activity and can be used with particularly good success for combating cereal diseases, such as, for example, against the powdery mildew of barley causative organism (*Erysiphe graminis*) or against the leaf spot disease of barley causative organism (*Pyrenophora teres*), against rust causative organisms or against the leaf spot disease on rice causative organism (*Pyricularia oryzae*). In addition, the active compounds according to the invention also exhibit an insecticidal and acaricidal activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractioned natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1:

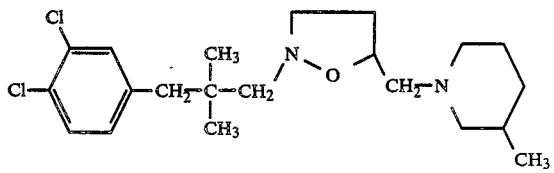

(Process a)

4 g (0.029 mol) of potassium carbonate in 20 ml of methanol are added to a mixture of 10.8 g (0.038 mol) of 3-(3,4-dichlorophenyl)-2,2-dimethylpropylhydroxylamine hydrochloride and 4 g (0.038 mol) of formalin (35 percent strength formaldehyde in water) in 100 ml of methanol, the potassium chloride which has precipitated out is filtered off and the filtrate is added at 100° C. to a solution of 11 g (0.076 mol) of 3-methyl-1-allylpiperidine in 200 ml of toluene such that the methanol slowly distils off. When all the methanol has been removed, the mixture is heated at the reflux temperature for 48 hours and the water is thereby removed via a water separator. The cooled reaction mixture is washed twice with water, dried over magnesium sulphate and concentrated in vacuo. The residue is purified by chromatography (silica gel; mobile phase: petroleum ether-/ethyl acetate 3:1).

4 g (26% of theory) of 2-[3-(3,4-dichlorophenyl)-2,2-dimethylprop-1-yl]-5-(3-methylpiperidin-1-yl-methyl)-isoxazolidine of refractive index $n_D^{20}$ 1.5267 are obtained.

Preparation of the starting compound:

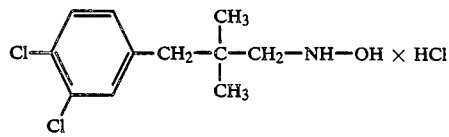

26 g (0.39 mol) of sodium cyanoborohydride are added in portions to a solution of 95 g (0.39 mol) of 3-(3,4-dichlorophenyl)-2,2-dimethyl-propionaldoxime in 1 l of methanol, which has been brought to pH 3 with hydrochloric acid against bromocresol green as an indicator, the pH value being kept between 3 and 5 by simultaneous addition of hydrochloric acid. When the addition has ended, the mixture is stirred at room temperature for 16 hours and is then brought to pH 1 by further addition of hydrochloric acid and concentrated in vacuo. The residue is taken up in chloroform/water and the chloroform phase is separated off, washed with water, dried over magnesium sulphate and freed from the solvent in vacuo.

77 g (70% of theory) of 3-(3,4-dichlorophenyl)-2,2-dimethylpropylhydroxylamine hydrochloride, which is further reacted without purification, are obtained.

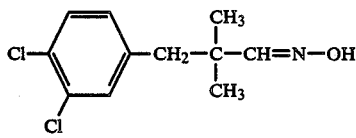

46 g (0.66 mol) of hydroxylamine hydrochloride are added in portions to a mixture of 147 g (0.63 mol) of 2-(3,4-dichlorophenyl)-2,2-dimethylpropionaldehyde and 100 g (2.5 mols) of sodium hydroxide in 800 ml of water. When the addition has ended, the mixture is subsequently stirred at room temperature for 16 hours and is then neutralized by addition of dry ice. The precipitate which has separated out is filtered off with suction, washed with water and dried.

142 g (92% of theory) of 3-(3,4-dichlorophenyl)-2,2-dimethyl-propionaldoxime of melting point 84° C. are obtained

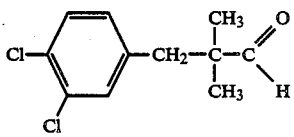

A mixture of 68.5 g (0.35 mol) of 3,4-dichlorobenzyl chloride and 36 g (0.5 mol) of isobutyraldehyde is slowly added dropwise to a mixture of 42 g (1.05 mols) of sodium hydroxide and 3 g of tetrabutylammonium iodide in 100 ml of water and 100 ml of toluene at 80° C. in the course of 5 hours, with vigorous stirring. When the addition has ended, the mixture is stirred at 80° C. for a further 3 hours, 200 ml of toluene are then added, the organic phase is washed three times with 100 ml of water each time, dried over sodium sulphate and concentrated in vacuo and the residue is distilled under a high vacuum.

57.9 g (73% of theory) of 2-(3,4-dichlorophenyl)-2,2-dimethyl-propionaldehyde of boiling point 92° C./0.13 mbar are obtained.

Example 2:

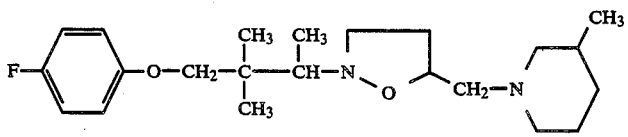

(Process b)

A mixture of 7 g (0.02 mol) of 5-bromomethyl-2-[4-(4-fluorophenoxy)-3,3-dimethyl-but-2-yl]isoxazolidine and 4 g (0.04 mol) of 3-methylpiperidine is stirred at 130° C. for 16 hours. For working up, the cooled reaction mixture is taken up in methylene chloride, washed with water, dried over sodium sulphate and concentrated in vacuo and the product is purified by chromatography (silica gel; mobile phase: petroleum ether/ethyl acetate 6:1).

4 g (51% of theory) of 2-[4-(4-fluorophenoxy)-3,3-dimethyl-but-2-yl]-5-(3-methylpiperidin-1-yl-methyl)-isoxazolidine of refractive index $n_D^{20}$ 1.5070 are obtained.

Preparation of the starting compounds

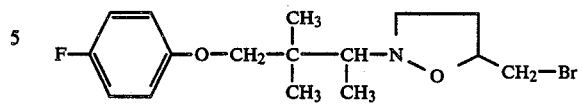

6.72 g (0.12 mol) of potassium hydroxide in 80 ml of methanol are added to a solution of 26.3 g (0.1 mol) of 4-(4-fluorophenoxy)-3,3-dimethyl-2-butyl-hydroxylamine hydrochloride in 80 ml of methanol, the potassium chloride which has precipitated out is filtered off and 10.3 g (0.12 mol) of formalin (35 percent strength aqueous formaldehyde solution) are added to the filtrate. This mixture is added dropwise at 70° C., with stirring, to a solution of 12.1 g (0.1 mol) of allyl bromide in 100 ml of carbon tetrachloride, to which 10 g of powdered molecular sieve have been added, the methanol slowly distilling off. At the end of the addition and the removal of the methanol by distillation, 4 ml (0.04 mol) of allyl bromide in 50 ml of carbon tetrachloride are added and the mixture is stirred at the reflux temperature for a further 16 hours. For working up, the cooled reaction mixture is washed with water, dried over sodium sulphate and concentrated in vacuo.

For purification, the residue is chromatographed over silica gel with petroleum ether/ethyl acetate 4:1.

7 g (20% of theory) of 5-bromomethyl-2-[4-(4-fluorophenoxy)-3,3-dimethyl-but-2-yl]-isoxazolidine are obtained as an oil. $^1$H—NMR*):δ=4.0–4.3 (m, 1H), 3.1–4.0 (m, 4H) ppm.

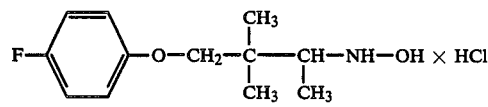

19.6 g (0.29 mol) of sodium cyanoborohydride (95%) are added in portions to a solution of 66.8 g (0.29 mol) of 2-hydroximino-3,3-dimethyl-4-(4-fluorophenoxy)-butane in 500 ml of methanol, which is kept at pH 3 with concentrated hydrochloric acid against bromocresol green. When the addition has ended, the pH value is kept at 3 with hydrochloric acid for a further 3 hours and the mixture is then subsequently stirred at room temperature for 16 hours. The reaction mixture is acidified to pH 1 and concentrated in vacuo. The residue is taken up in chloroform/water, the organic phase is separated off and dried over sodium sulphate and the solvent is distilled off in vacuo. 52.3 g (67.1% of theory) of 4-(4-fluorophenoxy)-3,3-dimethyl-2-butyl-hydroxylamine hydrochloride of melting point 99° C. are obtained.

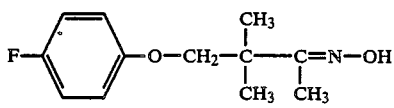

A solution of 40 g of sodium hydroxide in 80 ml of water is added dropwise to a mixture of 84 g (0.4 mol) of 3,3-dimethyl-4-(4-fluorophenoxy)-butan-2-one in 200 ml of ethanol and 28.3 g (0.41 mol) of hydroxylamine hydrochloride in 100 ml of water at 50° C. and the mixture is allowed to react at 60° C. for 16 hours. The reaction mixture is cooled and neutralized with dry ice. The solid which has precipitated is filtered off with suction and dried.

69 g (76.6% of theory) of 2-hydroximino-3,3-dimethyl-4-(4-fluorophenoxy)-butane of melting point 65° C.-66° C. are obtained.

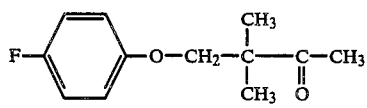

200 g (1 mol) of 4-methanesulphonyloxy-3,3-dimethyl-butan-2-one (compare, for example, DE-OS (German Published Specification) 2,843,767 or DE-OS (German Published Specification) 2,918,894) are added dropwise to a mixture of 112 g (1 mol) of 4-fluorophenol and 56 g (1 mol) of potassium hydroxide in 30 ml of water. When the addition has ended, the mixture is allowed to after-react at 110° C.-115° C. for 20 hours and is cooled, diluted with 1,000 ml of ethyl acetate and washed with 300 ml of water, two to three times with dilute aqueous sodium hydroxide solution and twice more with water, the organic phase is dried over sodium sulphate and concentrated in vacuo and the residue is distilled under a high vacuum.

159.6 g (76% of theory) of 4-(4-fluorophenoxy)-3,3-dimethyl-butan-2-one of boiling point b.p. 90° C./0.1 mbar are obtained.

The following aminomethylisoxazolidines of the general formula (I) are obtained in a corresponding manner and in accordance with the general statements on the preparation.

| Example No. | $R^1$ | $-N\begin{matrix}R^2\\R^3\end{matrix}$ | physical data |
|---|---|---|---|
| 3 | 3-F₃C-C₆H₄-CH₂-CH(CH₃)- | 2,6-dimethylmorpholino | $n_D^{20}$ 1.4825 |
| 4 | cyclohexyl | 3-methylpiperidino | b.p. 110° C./ 0,04 mbar |
| 5 | cyclohexyl | 3-methylpiperidino (× CH₃-C₆H₄-SO₃H) | $n_D^{20}$ 1.5182 |
| 6 | cyclohexyl | morpholino | $n_D^{20}$ 1.4984 |

-continued
$$\underset{R^1}{\overset{}{N}}\underset{O}{\overset{}{\diagdown}}\underset{}{\overset{}{\diagup}}CH_2-N\overset{R^3}{\underset{R^2}{\diagdown}}$$ (I)
| Example No. | R¹ | $-N\overset{R^2}{\underset{R^3}{\diagdown}}$ | physical data |
|---|---|---|---|
| 7 | 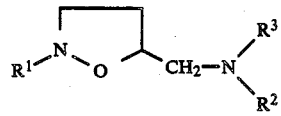 | 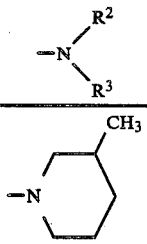 | $n_D^{20}$ 1.4903 |
| 8 | 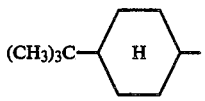 | 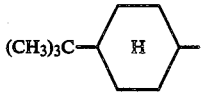 | $n_D^{20}$ 1.4931 |
| 9 |  | 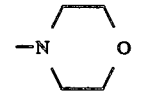 (× CH₃—⟨⟩—SO₃H) | ¹H—NMR*: 3.8–4.0; 3.1–3.6 |
| 10 | 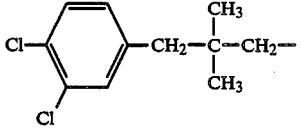 | 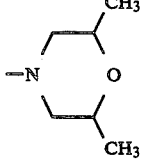 | $n_D^{20}$ 1.5253 |
| 11 | 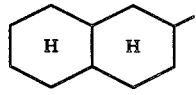 | 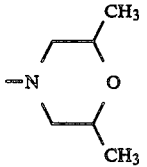 | $n_D^{20}$ 1.5021 |
| 12 | 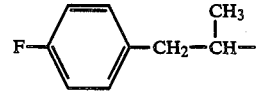 | 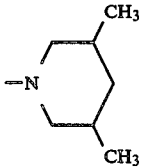 | $n_D^{20}$ 1.5033 |
| 13 | 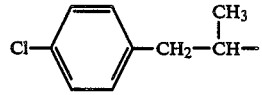 | 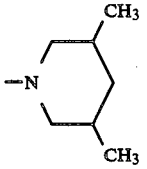 | $n_D^{20}$ 1.5226 |
| 14 | 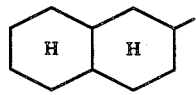 | 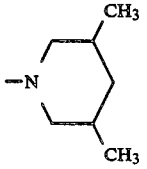 | $n_D^{20}$ 1.5027 |

-continued $$\begin{array}{c} R^1-N \\ \phantom{R^1-}O \end{array}\!\!\!\!\!\diagdown\!\!\!\!\!\begin{array}{c} \\ CH_2-N \end{array}\!\!\!\!\begin{array}{c} R^3 \\ R^2 \end{array}$$ (I)

| Example No. | R¹ | $-N\begin{array}{c}R^2\\R^3\end{array}$ | physical data |
|---|---|---|---|
| 15 | 4-F-C₆H₄-O-CH₂-C(CH₃)₂-CH(CH₃)- | 3,5-dimethylpiperidin-1-yl | $n_D^{20}$ 1.5035 |
| 16 | 4-F-C₆H₄-O-CH₂-C(CH₃)₂-CH(CH₃)- | piperidin-1-yl | $n_D^{20}$ 1.5107 |
| 17 | 4-(CH₃)₃C-C₆H₁₀- | 2,6-dimethylmorpholin-4-yl | $n_D^{20}$ 1.4859 |
| 18 | 4-(CH₃)₃C-C₆H₁₀- | 3,5-dimethylpiperidin-1-yl | $n_D^{20}$ 1.4884 |
| 19 | 4-(CH₃)₃C-C₆H₁₀- | piperidin-1-yl | $n_D^{20}$ 1.4880 |
| 20 | 3,4-Cl₂-C₆H₃-CH₂-C(CH₃)₂-CH₂- | 3,5-dimethylpiperidin-1-yl | $n_D^{20}$ 1.5268 |
| 21 | 3,4-Cl₂-C₆H₃-CH₂-C(CH₃)₂-CH₂- | morpholin-4-yl | $n_D^{20}$ 1.5380 |
| 22 | 4-(CH₃)₃C-C₆H₄-CH₂-CH(CH₃)- | 2,6-dimethylmorpholin-4-yl | $n_D^{20}$ 1.5118 |

-continued
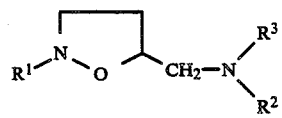 (I)
| Example No. | R¹ | −N(R²)(R³) | physical data |
|---|---|---|---|
| 23 | 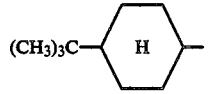 | 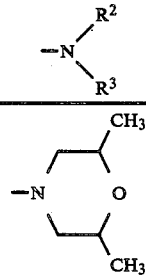 | M.p. 59° C.–60° C. |
| 24 | 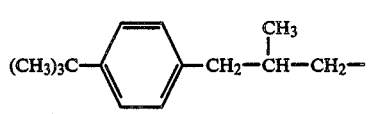 | 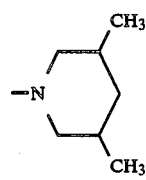 | $n_D^{20}$ 1.5108 |
| 25 | 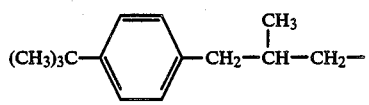 | 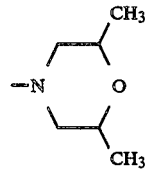 | $n_D^{20}$ 1.5089 |
| 26 | 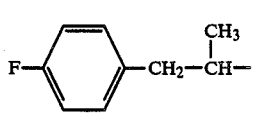 | 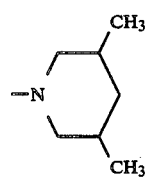 | $^1$H—NMR*: 4.6–4.9 |
| 27 | 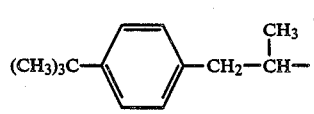 | 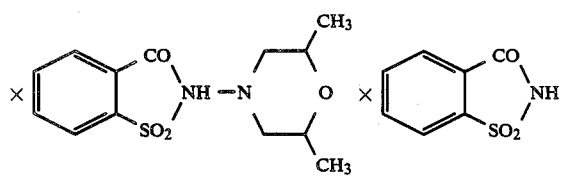 | $^1$H—NMR*: 4.2 |
| 28 | 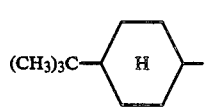 | 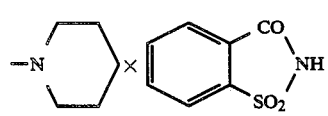 | $^1$H—NMR*: 4.7–4.9 |
| 29 | 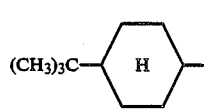 | 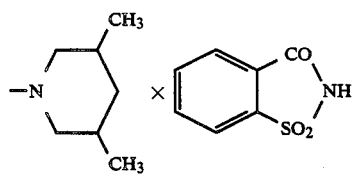 | $^1$H—NMR*: 4.7–4.8 |
| 30 | 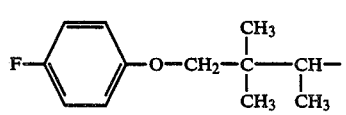 | 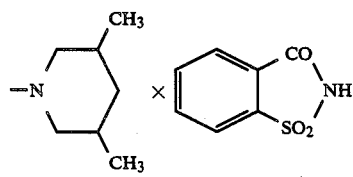 | $^1$H—NMR*: 4.6 |

-continued

| Example No. | R¹ | −N(R²)(R³) | physical data |
|---|---|---|---|
| 31 | 3-CF₃-C₆H₄-CH₂-CH(CH₃)- | 2,6-dimethylmorpholino × saccharin | $^1H$—NMR*: 4.6–4.9 |
| 32 | 2,6-dichlorobenzyl- | −NH-cyclohexyl | $n_D^{20}$ 1.5550 |
| 33 | 4-F-C₆H₄-O-CH₂-C(CH₃)₂-CH(CH₃)- | 3-methylpiperidino × 2-acetyl-benzisothiazole-1,1-dioxide | $^1H$—NMR: 0.9–1.1 6.8–7.0 7.55–7.8 |

*The $^1H$—NMR spectra were recorded in CDCl₃ with tetramethylsilane (TMS) as the internal standard. The chemical shift is stated as the δ value in ppm.

The $^1H$-NMR spectra were recorded in CDCL₃ with tetramethylsilane (TMS) as the internal standard. The chemical shift is stated as the δ value in ppm.

USE EXAMPLES

The compounds shown below were employed as comparison substances in the use examples which follow:

(A)
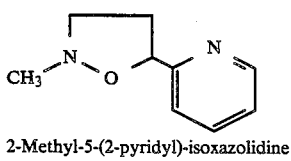

2-Methyl-5-(2-pyridyl)-isoxazolidine (B)
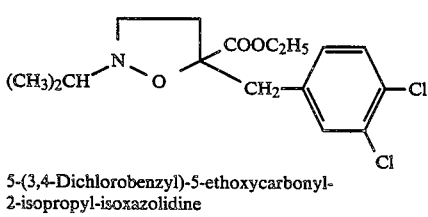

5-(3,4-Dichlorobenzyl)-5-ethoxycarbonyl-2-isopropyl-isoxazolidine (C)
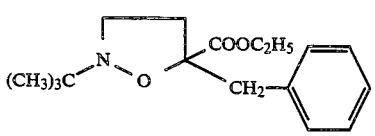

5-Benzyl-5-ethoxycarbonyl-2-t-butyl-isoxazolidine (all known from DE-OS (German Published Specification) 3,418,395)

Example A

Erysiphe test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the preparation Examples 1, 2, 3, 5, 6, 7, 8, 10, 11, 12, 13, 14, 15, 16, 17, 18, 19, 20, 21, 22 and 23.

Example B

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the preparation Examples 3, 8, 10, 16, 21, 22 and 23.

It is understood that the specification and examples are illustrative but not limitative of the present invention and that other embodiments within the spirit and scope of the invention will suggest themselves to those skilled in the art.

We claim:

1. An aminomethylisoxazolidine of the formula

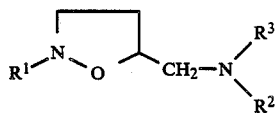

in which

R$^1$ represents arylalkyl, aryloxyalkyl or arylthioalkyl with in each case 6 to 10 carbon atoms in the aryl part and 1 to 10 carbon atoms in the straight-chain or branched alkyl part, optionally mono-substituted or poly-substituted in the aryl part by identical or different substituents selected from the group consisting of halogen, cyano, nitro, in each case straight-chain or branched alkyl, alkoxy, alkylthio, halogenoalkyl, halogenoalkoxy and halogenoalkylthio with in each case 1 to 6 carbon atoms and where appropriate 1 to 9 identical or different halogen atoms, amino and in each case straight-chain or branched alkylamino, dialkylamino and alkoximinoalkyl with in each case 1 to 4 carbon atoms in the individual alkyl parts, and R$^2$ and R$^3$, together with the nitrogen atom to which they are bonded, represent a saturated 5-to 7-membered heterocyclic radical which optionally can contain further hetero atoms, and is optionally monosubstituted or polysubstituted by identical or different substituents selected from the group consisting of in each case straight-chain or branched alkyl or hydroxyalkyl with in each case 1 to 4 carbon atoms.

2. An aminomethylisoxazolidine or salt according to claim 1.

in which

R$^1$ represents phenylalkyl, phenoxyalkyl or phenylthioalkyl with in each case 1 to 8 carbon atoms in the particular straight-chain or branched alkyl parts and optionally mono-, di- or trisubstituted in the phenyl part by identical or different substituents selected from the group consisting of fluorine, chlorine, bromine, straight-chain or branched alkyl with 1 to 6 carbon atoms, methoxy, ethoxy, n- or i-propoxy, n-, i-, s- or t-butoxy, methylthio, trfluoromethyl, trifluoromethoxy, trifluoromethylthio and methoximinomethyl, and R$^2$ and R$^3$, together with the nitrogen atom to which they are bonded, represent a heterocyclic radical of the formula

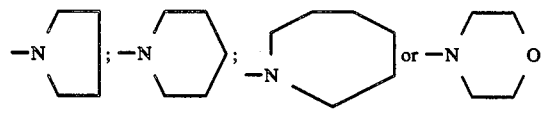

which is optionally mono-, di- or trisubstituted identically or differently by methyl, ethyl or hydroxymethyl.

3. A compound according to claim 1 wherein such compound is 2-[3-(4-fluorophenoxy)-1,2,2-trimethyl-prop-1-yl]-5-(piperidin-1-yl-methyl)-isoxazolidine of the formula

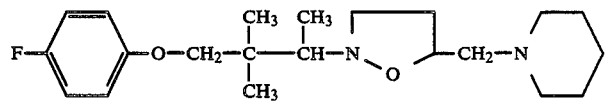

or an acid addition salt thereof.

4. A compound according to claim 1 wherein such compound is 2-[3-(3,4-dichlorophenyl)-2,2-dimethyl-prop-1-yl]-5-(morpholin-4-yl-methyl)-isoxazolidine of the formula

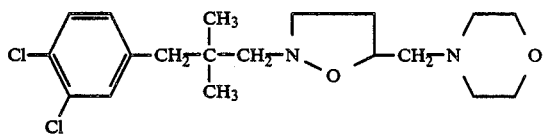

or an acid salt thereof.

5. A compound according to claim 1 wherein such compound is 2-[2-(4-t-butyl-phenyl)-1-methyl-ethyl]-5-(2,6-dimethyl-morpholin-4-yl-methyl)-isoxazolidine of the formula

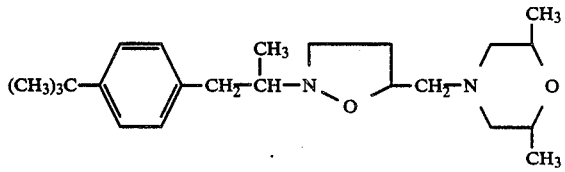

or an acid salt thereof.

6. A fungicidal composition comprising a fungicidally effective amount of a compound or salt according to claim 1 and a diluent.

7. A method of combating fungi which comprises applying to such fungi or to a fungus habitat a fungicidally effective amount of a compound or salt according to claim 1.

8. The method according to claim 7, wherein such compound is 2-[3-(4-fluorophenoxy)-1,2,2-trimethylprop-1-yl]-5-(piperidin-1-yl-methyl)-isoxazolidine,
2-[3,4-dichlorophenyl)-2,2-dimethylprop-1-yl]-5-(morpholin-4-yl-methyl)-isoxazolidine or
2-[2-(4-t-butyl-phenyl)-1-methyl-ethyl]-5-(2,6-dimethyl-morpholin-4-yl-methyl-isoxazolidine,
or an acid addition salt thereof.

* * * * *